(12) United States Patent
Falco

(10) Patent No.: US 6,568,394 B2
(45) Date of Patent: May 27, 2003

(54) FLANGED EARPLUG

(75) Inventor: Robert N. Falco, Indianapolis, IN (US)

(73) Assignee: Cabot Safety Intermediate Corporation, Newark, DE (US)

( * ) Notice: Subject to any disclaimer, the term of this patent is extended or adjusted under 35 U.S.C. 154(b) by 0 days.

(21) Appl. No.: 09/978,881

(22) Filed: Oct. 16, 2001

(65) Prior Publication Data

US 2002/0066455 A1 Jun. 6, 2002

Related U.S. Application Data

(60) Provisional application No. 60/240,212, filed on Oct. 13, 2001.

(51) Int. Cl.$^7$ ................................................ A61F 11/00
(52) U.S. Cl. .......................................... 128/864; 2/209
(58) Field of Search ................................. 128/864–868; 181/130, 129, 135; 2/7, 9, 10, 11, 171, 209

(56) References Cited

U.S. PATENT DOCUMENTS

| | | | | |
|---|---|---|---|---|
| 2,246,737 A | * | 6/1941 | Knudsen | 128/864 |
| 2,427,664 A | | 9/1947 | Dunbar et al. | 128/151 |
| 2,487,038 A | * | 11/1949 | Baum | 128/864 |
| 3,800,791 A | * | 4/1974 | Visor | 128/864 |
| D298,356 S | | 11/1988 | Falco | 24/67 |
| 4,867,149 A | | 9/1989 | Falco | 128/864 |

FOREIGN PATENT DOCUMENTS

| | | |
|---|---|---|
| DE | 28 08 525 | 10/1979 |
| FR | 75 518 E | 7/1961 |
| JP | 2000 201964 | 7/2000 |
| WO | WO 99 36016 | 10/1999 |

OTHER PUBLICATIONS

PCT Search Report, filed Oct. 16, 2001.

* cited by examiner

Primary Examiner—Michael A. Brown
(74) Attorney, Agent, or Firm—Cantor Colburn LLP

(57) ABSTRACT

A multi-flanged earplug is provided, comprising a stem, a rounded flange positioned at a first end of the stem, and at least a second flange positioned between the first end portion of the stem and an opposing second end portion of the stem. In one embodiment, the first flange is generally hemispherical in shape and has a curvature that is generally is generally convex with respect to the tip of the first end portion of the stem, while the second flange has a shape that is generally concave with respect to the tip of the first end portion of the stem. In another embodiment, an outer circumference portion of the second flange has an increased thickness relative to an inner, annular portion of the second flange. In another embodiment, an outer circumference portion of the second flange is provided with a protruding ridge.

12 Claims, 4 Drawing Sheets

FLANGED EARPLUG

CROSS REFERENCE TO RELATED APPLICATIONS

The present application claims priority to provisional application serial No. 60/240,212, filed Oct. 13, 2001, the entirety of which is specifically incorporated herein by reference.

BACKGROUND

Multiple flanged earplugs are well known in the art. For example, a three flanged earplug composed of a resilient, soft polymeric material is described in U.S. Pat. No. 4,867,149 to Falco, which is assigned to the assignee hereof and incorporated herein by reference in its entirety.

However, substantial room for improvement exists in the art, specifically with regard to fit, comfort and efficiency of hearing protection. Accordingly, a novel and improved multi-flange earplug is provided as described below.

SUMMARY

The drawbacks and deficiencies of the prior art are overcome or alleviated by the present improved multi-flanged earplug, comprising a stem, a rounded flange positioned at a first end of the stem, and at least a second flange positioned between the first end portion of the stem and an opposing second end portion of the stem. In one embodiment, the first flange is generally hemispherical in shape and has a curvature that is generally is generally convex with respect to the tip of the first end portion of the stem, while the second flange has a shape that is generally concave with respect to the tip of the first end portion of the stem. In another embodiment, an outer circumference portion of the second flange has an increased thickness relative to an inner, annular portion of the second flange. In another embodiment, an outer circumference portion of the second flange is provided with a protruding ridge.

The above-described and other features and advantages of the present improved flanged earplug will be appreciated and understood by those skilled in the art from the following detailed description and drawings.

BRIEF DESCRIPTION OF THE DRAWINGS

Referring now to the drawings, wherein like elements are numbered alike in the several figures.

DETAILED DESCRIPTION

Figure 1:
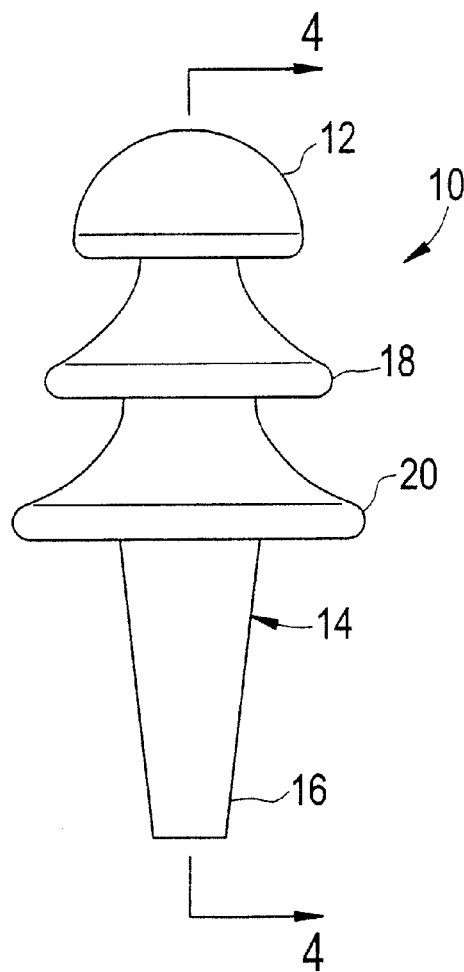
FIG. 1 is a front plan view of an embodiment of the present improved flanged earplug.
Figure 2:
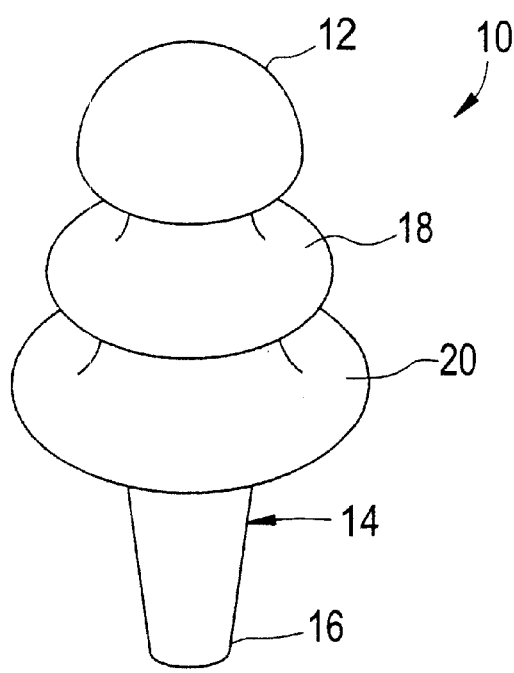
FIG. 2 is a top corner view thereof.
Figure 3:
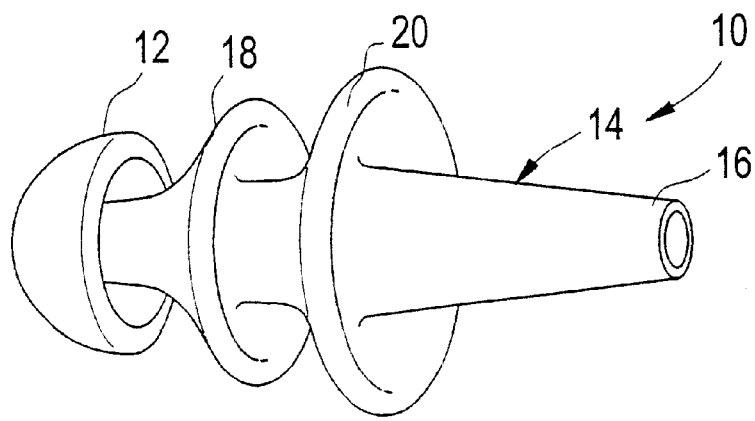
FIG. 3 is a side perspective view thereof.

Referring now to FIGS. 1–3, perspective views of an exemplary first embodiment of the present improved flanged earplug 10 are illustrated. The earplug is shown generally at 10 and comprises a rounded first flange 12, which is positioned at one end of a stem 14. In the illustrated embodiment, second and third flanges 18 and 20, respectively, are positioned on the stem between the first flange 12 and the opposing stem end portion 16.

Figure 4:
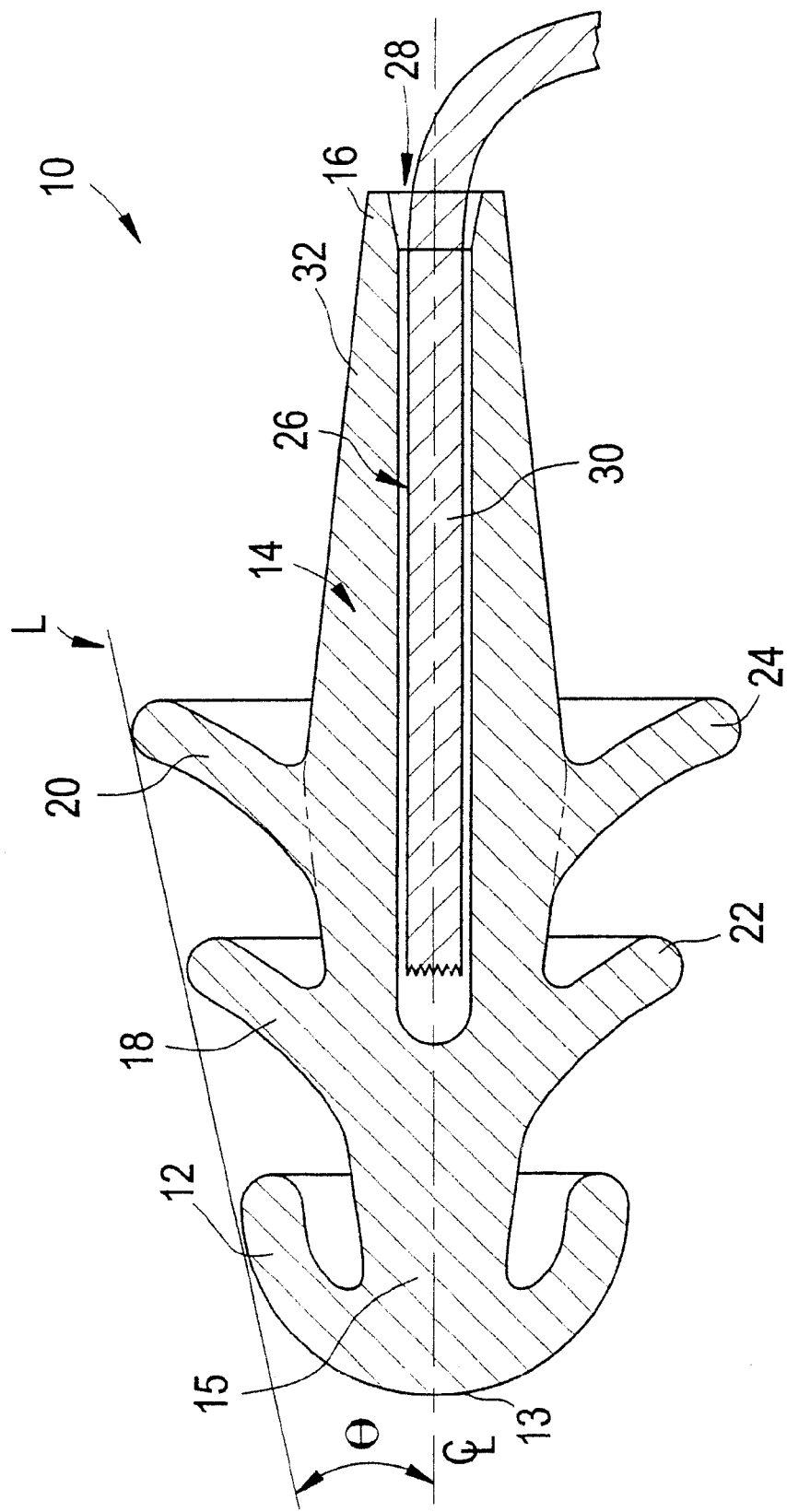
FIG. 4 is a cross-sectional elevation view along the line 4—4 of FIG. 1.

In one exemplary embodiment, as shown in FIG. 4, the first flange 12 has a generally hemispherical shape. In another exemplary embodiment, the first flange extends rearwardly from its point of attachment to the stem 14 in a convexly arcuate manner, with respect to the tip 13 of the first end portion 15 of the stem 14, and in a generally hemispherical conformation. Thus, the first flange 12 extends outwardly and rearwardly from a first end portion 15 of the stem 14, thereby to define an approximately uniform skirt on at least a substantial portion of the rearward region of the first flange 12. In an exemplary embodiment, the diameter of the stem 14 proximate to the skirt of the first flange 12 is of a diameter so as to provide an annular free space between the inner surface of the skirt of the first flange 12 and the stem 14 such that the skirt may collapse into and occupy said space upon insertion of the earplug 10 into the ear canal.

In another exemplary embodiment, the first flange 12 defines between about 45 degrees to about 55 degrees of a chordally sectioned hollow spherical body whose external surface is, at a majority of points thereon, equidistant from the single geometric center thereof.

As best seen in FIG. 4, the second and third flanges extend radially outwardly from the stem 14 to rounded edges 22 and 24, respectively. In one embodiment the first flange 12 is generally hemispherical in shape while the second and third flanges 18, 20, which are between a first end portion 15 of the stem 14 and the opposing end portion 16 of the stem 14, have curvatures that are generally opposite in direction with respect to the curvature of the first flange 12 and that are generally concave with respect to the tip 13 of the first end portion 15 of the stem 14.

Referring to FIG. 4, the illustrated earplug 10 includes a stem 14 taper beginning with the rounded flange 12. From the rounded flange 12, the stem 14 tapers outwardly to about a middle portion of the stem 14, whereupon it tapers inwardly to a smaller diameter at the opposing end 16. Second and third flanges 18, 20 are shown to be positioned on the section of the stem 14 that tapers outwardly and which includes the rounded flange 12.

With reference to FIG. 4, it is also to be noted that the stem tapers outwardly from the first flange 12 to a point on the stem past flanges 18 and 20. In the illustrated exemplary embodiment, the flanges 12, 18 and 20 are spaced along the length of stem 14 such that, in the finished earplug 10, a single straight line of construction, L, can be drawn so as to be in at least point contact with an edge of all flanges 12, 18 and 20 of the array. In one embodiment, the diameters and spacings of the flanges 12, 18 and 20 are selected such that the half-angle $\theta$ defined between said line of construction L and a forwardly extended centerline $C_L$, or longitudinal axis, of the stem 14 will reside within the range of between 10 degrees and 16 degrees. In another embodiment, the half angle $\theta$ resides within the range of 12 degrees and 14 degrees. By adherence to these dimensions it is assured that the earplug constructed in accordance therewith will be utilizable by and effective for the great majority of the user population.

Figure 5:
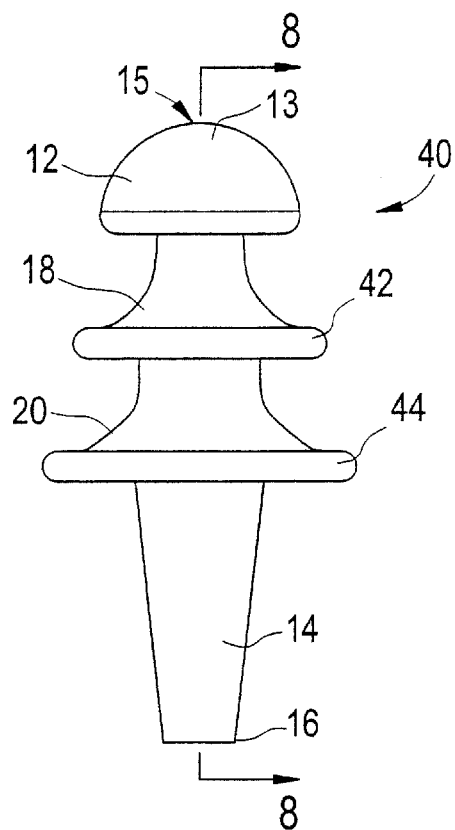
FIG. 5 is a front plan view of a second embodiment of the present improved flanged earplug.
Figure 6:
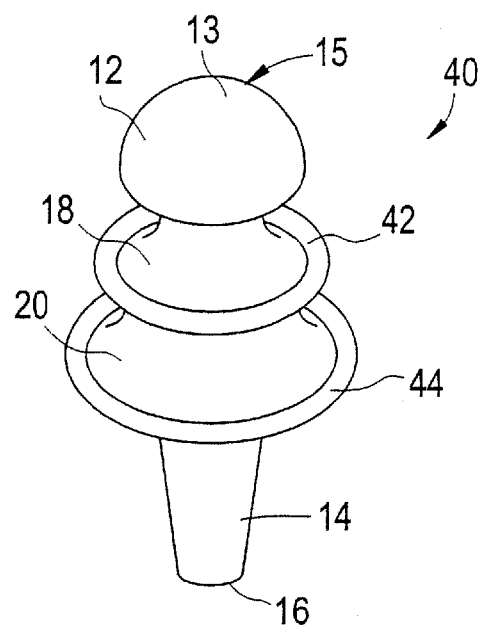
FIG. 6 is a top corner view thereof.
Figure 7:
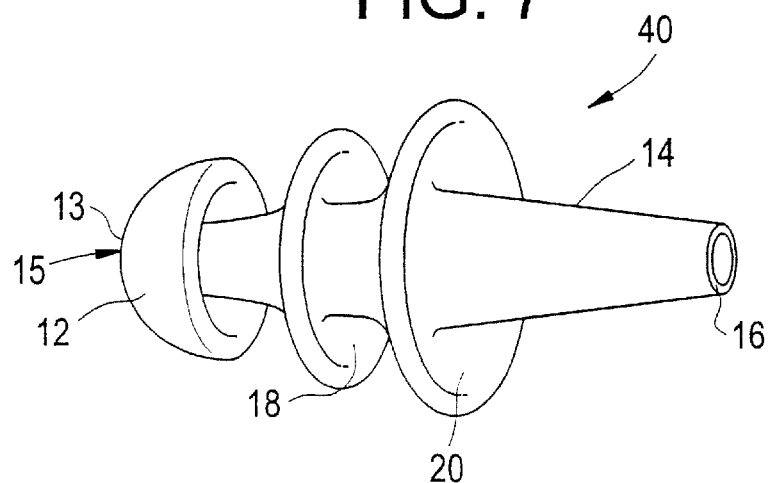
FIG. 7 is a side perspective view thereof.

Turning now to FIGS. 5–7, perspective views of another exemplary embodiment of the present improved flanged earplug 40 are illustrated. The earplug is shown generally at 40 and comprises a rounded first flange 12, which is positioned at one end of a stem 14. In the illustrated embodiment, second and third flanges 18 and 20, respectively, are positioned on the stem between the first flange 12 and the opposing stem end portion 16.

Figure 8:
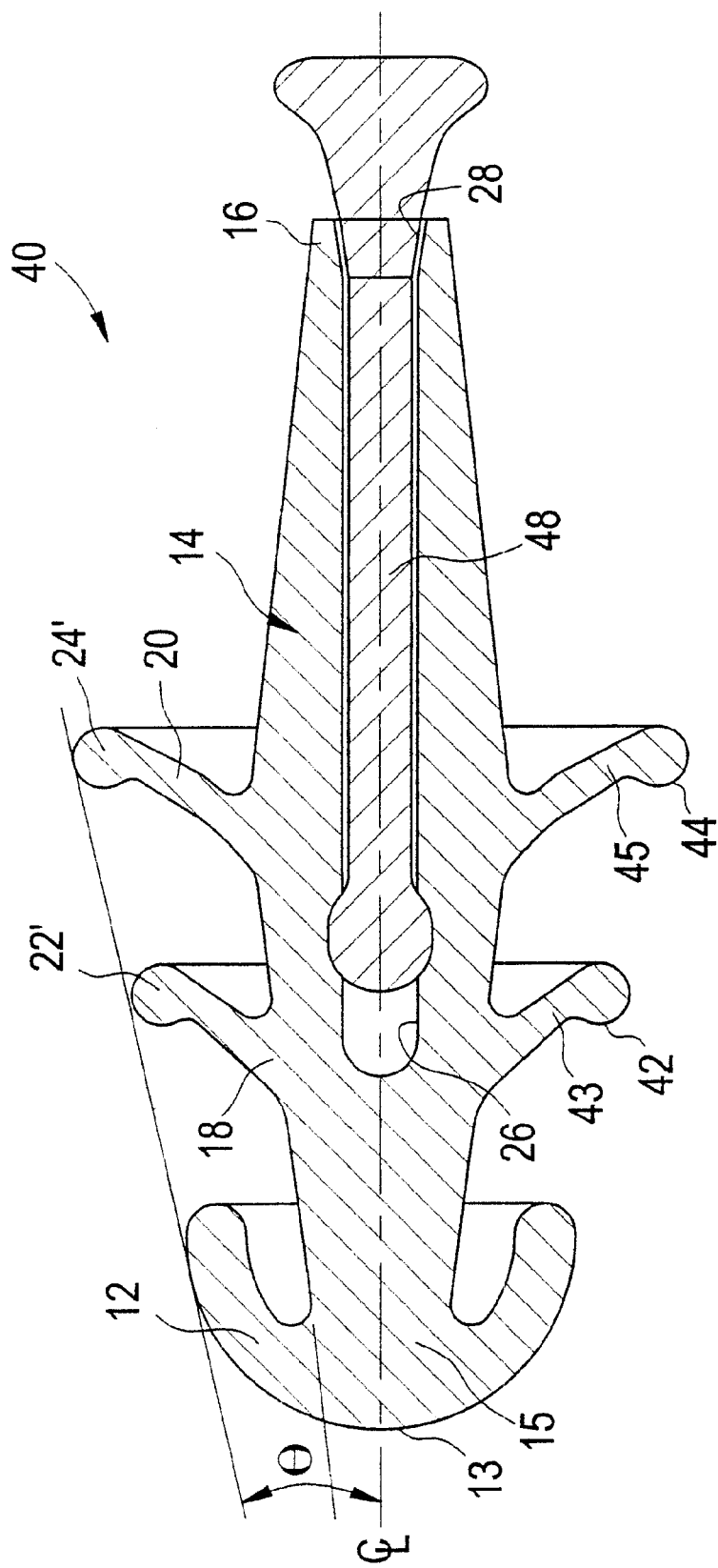
FIG. 8 is a cross-sectional elevation view along the line 8—8 of FIG. 5.

In one exemplary embodiment, as shown in FIG. 8, the first flange 12 has a generally hemispherical shape. In another exemplary embodiment, the first flange extends rearwardly from its point of attachment to the stem 14 in a convexly arcuate manner, with respect to the tip 13 of the first end portion 15 of the stem 14, and in a generally hemispherical conformation. Thus, the first flange 12 extends outwardly and rearwardly from a first end portion 15 of the stem 14, thereby to define an approximately uniform skirt on at least a substantial portion of the rearward region of the first flange 12.

As best seen in FIG. 8, the second and third flanges extend radially outwardly from the stem 14 to rounded, outer circumference portions 22' and 24', respectively. In one embodiment and as shown in FIG. 8, the outer circumference portion 22' of the second flange 18 has an increased thickness relative to an inner, annular portion 43 of the second flange 18. Similarly, the outer circumference portion of the third flange has an increased thickness relative to an inner, annular portion 45 of the third flange 20. In another embodiment, as can be seen in the perspective views of FIGS. 5–6, an outer circumference portions 22', 24' of the second and third flanges 18, 20 are provided with protruding ridges 42, 44. With referenced to the illustrated embodiment in FIG. 8, the ridges are rounded portions of the outer circumference portions 22', 24', the rounded portions of which have a substantially circular cross-section.

In one embodiment the first flange 12 is generally hemispherical in shape while the second and third flanges 18, 20, which are between a first end portion 15 of the stem 14 and the opposing end portion 16 of the stem 14, have curvatures that are generally opposite in direction with respect to the curvature of the first flange 12 and that are generally concave with respect to the tip 13 of the first end portion 15 of the stem 14.

Referring still to FIG. 8, the illustrated earplug 10 includes a stem 14 taper beginning with the rounded flange 12. From the rounded flange 12, the stem 14 tapers outwardly to about a middle portion of the stem 14, whereupon it tapers inwardly to a smaller diameter at the opposing end 16. Second and third flanges 18, 20 are shown to be positioned on the section of the stem 14 that tapers outwardly and which includes the rounded flange 12.

Referring to FIGS. 4 and 8, the stem 14 includes a longitudinal bore 26 therethrough, which terminates at a flared opening 28. The bore 26 is dimensioned so as to receive a cord 30 (illustrated in FIG. 4) such that a pair of the present earplugs may be positioned on either end of the cord 30. It is often desirable to provide pairs of earplugs 10 tethered together by means of a length of pliant cord 30. Such a tethered earplug construction can serve to prevent accidental dropping or loss thereof. This can be of importance, for instance, where the earplugs are to be utilized in an industrial food processing environment or in an environment wherein a dropped earplug would be likely to be so dirtied as to be rendered unusable or to be lost altogether. The cord 30 can be secured in the bore 26 by any suitable means, such as by solvent or thermal welding thereof or by use of a suitable adhesive or by use of a cord whose ends are of somewhat greater diameter than the diameter of the bore 26, thereby to cause the resilient material surrounding said bore 26 to resiliently grasp the cord ends in a secure manner. For further general details relating to tethered earplug constructions reference may be had to such literature as: U.S. Pat. No. D-241,881, to Peterson et al.; U.S. Pat. No. 4,193,396, to Wacker; U.S. Pat. No. 4,219,018, to Draper, Jr.; U.S. Pat. No. D-245,202, to Asker.

Additionally, the present earplugs may also be utilized as stopple elements of a hearing protector device comprising a generally U-shaped spring headband to the free ends of which headband the stopple elements are affixed in an inwardly directed manner. In this embodiment, the earplugs of the invention are inserted into the ear canals of the wearer and are maintained under the continuous inwardly directed biasing forces of the spring headband. Further details relating to hearing protectors of this general type can be had by reference to such literature as U.S. Pat. No. 4,461,290, to Gardner, Jr. et al., or U.K. Pat. No. 1,355,052, to Metal Box Company, Limited.

Exemplary materials for the earplug 10 include, but are not limited to soft polymeric materials having a variety of possible Shore A durometer hardnesses, such as that described in the aforementioned U.S. Pat. No. 4,867,149 to Falco. In one exemplary embodiment, the earplug 10 comprises a resilient polymeric material. There are many known resilient polymeric materials which may be utilized effectively in the fabrication of the earplugs of the invention. In one embodiment, polymeric materials are employed, including thermoplastic elastomer (TPE) compositions. In another embodiment, a thermoplastic elastomer having a Shore A durometer of between about 13 and 17 is employed. In another exemplary embodiment, construction of the earplugs of the invention is from a thermoplastic SBR block copolymer such as produced and sold in a number of grades under the brand name, DYNAFLEX, by GLS Corporation, Chicago, Ill. In another embodiment, a silicone modified thermoplastic SBR block copolymer is utilized, such as exemplified by a family of thermoplastic copolymers sold under the trademark, C-FLEX®, Concept Polymer Technologies, Inc., Clearwater, Fla.

The stem 14 can comprise a resilient material of the same type employed for the flange 12, 18 and 20 or, if desired, can comprise a resilient material having a somewhat higher Shore A Durometer hardness value of, for example, 100. In one embodiment, for purposes of easy fabrication, a single resilient material is utilized for the entirety of the construction, the material having a Shore A durometer hardness of between about 13 and 17. Where increased longitudinal stiffness is desired, particularly with stems having lower Shore A durometer hardnesses, it may be desirable to increase the diameter of the stem 12 relative relative to the diameters of the respective flanges 12, 18 and 20 and/or to incorporate a stem stiffener 48 (an exemplary embodiment of which is shown in FIG. 8) into the earplug 10.

The earplug 10 can be fabricated by any suitable polymer molding technique, such as by injection molding thereof.

In order that the earplugs 10 can be readily inserted and removed from the ear canal, it is desirable that the stem 14 extend rearwardly to a convenient length beyond the circumferential edge 24, 24' of the third flange 20 such that the rearmost portion thereof defines a handle 32 to be readily grasped between the thumb and forefinger of the user.

It will be apparent to those of skill in the art that many of the functional benefits of the present invention arise, at least in part, because the flanges 12, 18 and 20 of the construction are embued with the ability to resiliently deform, in use, to the extent necessary under relatively small and essentially linear forces exerted by or reflected into the walls of the ear canal upon insertion of the earplug thereinto. Thus, there exists a complex interplay between the specific geometries and sizing of the elements of the earplug construction taken in combination with the hardness(es) of the resilient polymeric material(s) of construction employed therefor.

While exemplary embodiments have been shown and described, various modifications and substitutions may be made thereto without departing from the spirit and scope of the invention. Accordingly, it is to be understood that the present invention has been described by way of illustration and not limitation.

What is claimed is:

1. A multi-flange earplug, comprising:
   a stem;
   a first flange positioned at a first end portion of the stem, the first flange having a generally hemispherical shape that is generally convex with respect to the tip of the first end portion of the stem;
   a second flange positioned between the first flange and a second end portion of the stem, the second flange having a shape that is generally concave with respect to the tip of the first end portion of the stem.

2. The multi-flange earplug in accordance with claim 1, further comprising a third flange positioned between the second flange and the second end portion of the stem, the third flange having a shape that is generally concave with respect to the tip of the first end portion of the stem.

3. The multi-flange earplug of claim 2, wherein an array of the first, second and third flanges are spaced apart and have sufficient outer diameters to form a single substantially straight line of construction so as to be in at least point contact with an edge of each of the first, second and third flanges.

4. The multi-flange earplug of claim 3, wherein a half angle defined between said line of construction and between a longitudinal axis of the stem is between about 10 degrees and about 16 degrees.

5. The multi-flange earplug of claim 4, wherein the half angle defined between said line of construction and between said longitudinal axis of the stem is between about 12 and about 14 degrees.

6. The multi-flange earplug in accordance with claim 1, wherein the first flange defines between about 45 degrees to about 55 degrees of a chordally sectioned hollow spherical body whose external surface is, at a majority of points thereon, equidistant from a single geometric center thereof.

7. The multi-flange earplug in accordance with claim 1, wherein the first flange extends outwardly and rearwardly from the first end portion of the stem to define an approximately uniform skirt on at least a substantial portion of the rearward region of the first flange.

8. The multi-flange earplug of claim 1, wherein the stem member is tapered outwardly from the first end portion of the stem to a point rearward from the first flange, and wherein the stem is tapered inwardly from said point rearward from the first flange to the second end portion of the stem.

9. The multi-flange earplug of claim 1, wherein the stem member includes a bore having an opening at the second end portion of the stem, and wherein the bore is dimensioned so as to receive a cord.

10. The multi-flange earplug of claim 1, wherein the earplug generally comprises a resilient polymeric material.

11. The multi-flange earplug of claim 10, wherein the earplug generally comprises a thermoplastic elastomer having a Shore A durometer of between about 13 and 17.

12. The multi-flange earplug of claim 11, wherein the stem member includes a bore having an opening at the second end portion of the stem, and wherein the earplug further includes a stem stiffener disposed within said bore.

* * * * *